(12) United States Patent
Vanden Hoek et al.

(10) Patent No.: US 7,235,042 B2
(45) Date of Patent: Jun. 26, 2007

(54) APPARATUS AND METHOD FOR APPLYING CARDIAC SUPPORT DEVICE

(75) Inventors: John Vanden Hoek, Elk River, MN (US); Jody Rivers, Elk River, MN (US); John David Dockter, Brooklyn Park, MN (US)

(73) Assignee: Acorn Cardiovascular, Inc., St. Paul, MN (US)

( * ) Notice: Subject to any disclaimer, the term of this patent is extended or adjusted under 35 U.S.C. 154(b) by 464 days.

(21) Appl. No.: 10/663,623

(22) Filed: Sep. 16, 2003

(65) Prior Publication Data

US 2005/0059854 A1  Mar. 17, 2005

(51) Int. Cl.
*A61F 13/00* (2006.01)
(52) U.S. Cl. .......................... 600/16; 600/37
(58) Field of Classification Search ............... 600/16, 600/37
See application file for complete search history.

(56) References Cited

U.S. PATENT DOCUMENTS

| | | | |
|---|---|---|---|
| 3,587,567 A | 6/1971 | Schiff | |
| 3,983,863 A | 10/1976 | Janke et al. | |
| 4,048,990 A | 9/1977 | Goetz | |
| 4,403,604 A | 9/1983 | Wilkinson et al. | |
| 4,428,375 A | 1/1984 | Ellman | |
| 4,630,597 A | 12/1986 | Kantrowitz et al. | |
| 4,690,134 A | 9/1987 | Snyders | |
| 4,821,723 A | 4/1989 | Baker, Jr. et al. | |
| 4,827,932 A | 5/1989 | Ideker et al. | |
| 4,834,707 A | 5/1989 | Evans | |
| 4,878,890 A | 11/1989 | Bilweis | |
| 4,936,857 A | 6/1990 | Kulik | |

(Continued)

FOREIGN PATENT DOCUMENTS

DE            324524           8/1920

(Continued)

OTHER PUBLICATIONS

"Abstracts From the 68th Scientific Sessions, Anaheim Convention Center, Anaheim, California," *American Heart Association Supplement to Circulation*, vol. 92, No. 8, Abstracts 1810-1813 (Oct. 15, 1995).

(Continued)

*Primary Examiner*—George Manuel
*Assistant Examiner*—Nicole R. Kramer
(74) *Attorney, Agent, or Firm*—Faegre & Benson LLP

(57) ABSTRACT

A method for applying a cardiac support device to a heart of a mammal includes surgically accessing a heart, providing a cardiac support device including a jacket, and positioning the jacket around at least a portion of the heart by applying a pulling force to the jacket. The step of positioning the jacket can include using a tool from a position superior to the heart to pull the jacket onto the heart. One device for placing a cardiac support jacket onto the heart includes first and second tubular walls. The second tubular wall is oriented within the first tubular wall and against an internal surface of the first tubular wall. The second tubular wall includes a plurality of grooves and has an open interior volume to hold the cardiac support jacket. Another device for placing a cardiac support jacket onto the heart includes a tubular wall having a plurality of lumens extending between opposite ends of the tubular wall.

16 Claims, 15 Drawing Sheets

U.S. PATENT DOCUMENTS

| | | | |
|---|---|---|---|
| 4,957,477 A | | 9/1990 | Lundback |
| 4,973,300 A | * | 11/1990 | Wright ........................ 600/37 |
| 4,976,730 A | | 12/1990 | Kwan-Gett |
| 5,057,117 A | | 10/1991 | Atweh |
| 5,087,243 A | | 2/1992 | Avitall |
| 5,131,905 A | | 7/1992 | Grooters |
| 5,150,706 A | | 9/1992 | Cox et al. |
| 5,186,711 A | | 2/1993 | Epstein |
| 5,192,314 A | | 3/1993 | Daskalakis |
| 5,256,132 A | | 10/1993 | Snyders |
| 5,290,217 A | | 3/1994 | Campos |
| 5,341,815 A | | 8/1994 | Cofone et al. |
| 5,356,432 A | | 10/1994 | Rutkow et al. |
| 5,366,460 A | | 11/1994 | Eberbach |
| 5,383,840 A | | 1/1995 | Heilman et al. |
| 5,385,156 A | | 1/1995 | Oliva |
| 5,405,360 A | | 4/1995 | Tovey |
| 5,429,584 A | | 7/1995 | Chiu |
| 5,507,779 A | | 4/1996 | Altman |
| 5,524,633 A | | 6/1996 | Heaven et al. |
| 5,603,337 A | | 2/1997 | Jarvik |
| 5,647,380 A | | 7/1997 | Campbell et al. |
| 5,702,343 A | | 12/1997 | Alferness |
| 5,713,954 A | | 2/1998 | Rosenberg et al. |
| 5,735,290 A | * | 4/1998 | Sterman et al. .............. 128/898 |
| 5,766,216 A | | 6/1998 | Gangal et al. |
| 5,800,334 A | | 9/1998 | Wilk |
| 5,800,528 A | | 9/1998 | Lederman et al. |
| 5,928,250 A | | 7/1999 | Koike et al. |
| 5,961,440 A | | 10/1999 | Schweich, Jr. et al. |
| 5,990,378 A | | 11/1999 | Ellis |
| 6,076,013 A | | 6/2000 | Brennan et al. |
| 6,077,218 A | | 6/2000 | Alferness |
| 6,085,754 A | | 7/2000 | Alferness et al. |
| 6,123,662 A | | 9/2000 | Alferness et al. |
| 6,126,590 A | | 10/2000 | Alferness |
| 6,155,968 A | | 12/2000 | Wilk |
| 6,155,972 A | | 12/2000 | Nauertz et al. |
| 6,165,121 A | | 12/2000 | Alferness |
| 6,165,122 A | | 12/2000 | Alferness |
| 6,169,922 B1 | | 1/2001 | Alferness et al. |
| 6,174,279 B1 | | 1/2001 | Girard |
| 6,179,791 B1 | | 1/2001 | Krueger |
| 6,193,648 B1 | | 2/2001 | Krueger et al. |
| 6,230,714 B1 | | 5/2001 | Alferness et al. |
| 6,241,654 B1 | | 6/2001 | Alferness |
| 6,293,906 B1 | | 9/2001 | Vanden Hoek et al. |
| 6,375,608 B1 | | 4/2002 | Alferness |
| 6,416,459 B1 | | 7/2002 | Haindl |
| 6,425,856 B1 | | 7/2002 | Shapland et al. |
| 6,482,146 B1 | | 11/2002 | Alferness et al. |
| 6,537,203 B1 | | 3/2003 | Alferness et al. |
| 6,544,168 B2 | | 4/2003 | Alferness |
| 6,569,082 B1 | | 5/2003 | Chin |
| 6,572,533 B1 | | 6/2003 | Shapland et al. |
| 6,579,226 B2 | | 6/2003 | Vanden Hoek et al. |

FOREIGN PATENT DOCUMENTS

| | | |
|---|---|---|
| DE | 38 31 540 A1 | 4/1989 |
| DE | 38 31 540 C2 | 6/1993 |
| DE | 295 17 393 U1 | 3/1996 |
| EP | 0 280 564 A2 | 8/1988 |
| EP | 0 303 719 A1 | 2/1989 |
| EP | 0 557 964 A1 | 9/1993 |
| GB | 2 209 678 A | 5/1989 |
| JP | 60-203250 | 10/1985 |
| JP | 01-145066 | 6/1989 |
| JP | 2271829 | 11/1990 |
| SU | 1009457 | 4/1983 |
| WO | WO 93/03685 | 3/1993 |
| WO | WO 96/16601 | 6/1996 |
| WO | WO 96/31175 | 10/1996 |
| WO | WO 98/29041 | 7/1998 |
| WO | WO 98/35632 | 8/1998 |
| WO | WO 98/58598 | 12/1998 |
| WO | WO 99/44534 | 9/1999 |
| WO | WO 00/02500 | 1/2000 |
| WO | WO 01/67985 A1 | 9/2001 |

OTHER PUBLICATIONS

Capomolla et al., "Dobutamine and nitroprusside infusion in patients with severe congestive heart failure: Hemodynamic improvement by discordant effects on mitral regurgitation, left atrial function, and ventricular function," *American Heart Journal*, vol. 134, No. 6, pp. 1089-1098 (Dec. 1997).

Capouya et al., "Girdling Effect of Nonstimulated Cardiomyoplasty on Left Ventricular Function," *Ann. Thorac. Surg.*, vol. 56, pp. 867-871 (1993).

Cohn, "The Management of Chronic Heart Failure." *The New England Journal of Medicine*, vol. 335, No. 7, pp. 490-498 (Aug. 15, 1996).

Coletta et al., "Prognostic value of left ventricular volume reponse during dobutamine stress echocardiography," *European Heart Journal*, vol. 18, pp. 1599-1605 (Oct. 1997).

DeVries, G. et al., "A Novel Technique for Measurement of Pericardial Pressure," *Am. J. Physiol. Heart Circ. Physiol.*, vol. 280, No. 6, pp. H2815-H2822 (Jun. 2001).

Guasp, "Una protesis contentiva para el tratamiento de la miocardiopatia dilatada," *Revista Espanola de Cardiologia*, vol. 51, No. 7, pp. 521-528 (Jul. 1998).

Hamilton, D. et al., "Static and Dynamic Operating Characteristics of a Pericardial Balloon," *J. Appl. Physiol.*, vol. 90, No. 4, pp. 1481-1488 (Apr. 2001).

Kass et al., "Reverse Remodeling From Cardiomyoplasty in Human Heart Failure," *Circulation*, vol. 91, No. 9, pp. 2314-2318 (May 1, 1995).

Levin et al., "Reversal of Chronic Ventricular Dilation in Patients With End-Stage Cardiomyopathy by Prolonged Mechanical Unloading, " *Circulation*, vol. 91, No. 11, pp. 2717-2720 (Jun. 1, 1995).

Oh et al., "The Effects Of Prosthetic Cardiac Binding And Adynamic Cardiomyoplasty In A Model Of Dilated Cardiomyopathy," *The Journal of Thoracic and Cardiovascular Surgery*, vol. 116, No. 1, pp. 148-153 (Jul. 1998).

Paling, "Two-Bar Fabrics (Part-Set Threading)," *Warp Knitting Technology*, Columbine Press (Publishers) Ltd., Buxton, Great Britain, p. 111 (1970).

Vaynblat et al., "Cardiac Binding in Experimental Heart Failure," *Ann Thorac Surg*, vol. 64, pp. 81-85 (1997).

\* cited by examiner

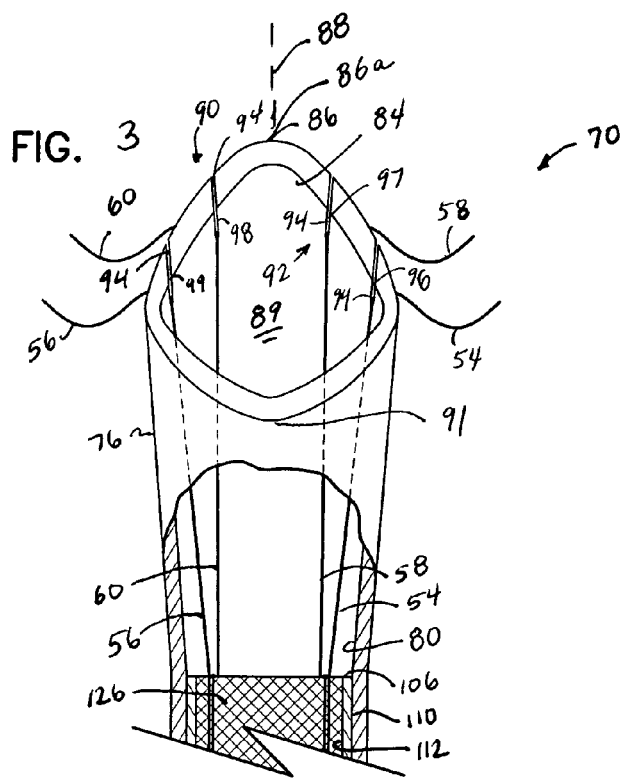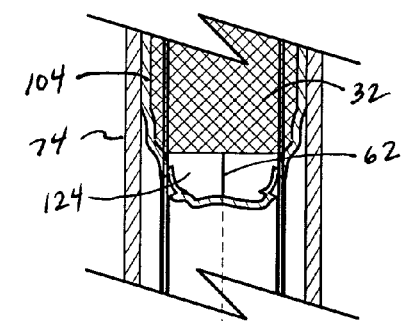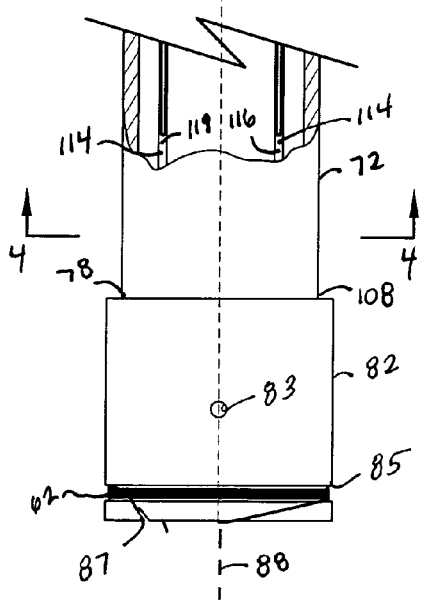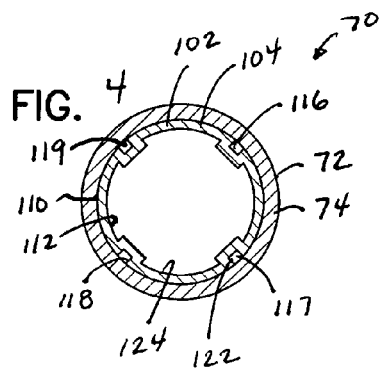

APPARATUS AND METHOD FOR APPLYING CARDIAC SUPPORT DEVICE

TECHNICAL FIELD

This disclosure relates to apparatus and methods for treating heart disease, particularly congestive heart disease, and related heart dysfunctions. More particularly, this disclosure relates to apparatus and methods for applying a cardiac support device to a heart.

BACKGROUND

Congestive heart disease is a progressive and debilitating illness. The disease is characterized by a progressive enlargement of heart. As the heart enlarges, the heart is performing an increasing amount of work in order to pump blood for each heart beat. In time, the heart becomes so enlarged that the heart cannot adequately supply blood. An afflicted patient is fatigued, unable to perform even simple exerting tasks and experiences pain and discomfort. Further, as the heart enlarges, the internal heart valves cannot adequately close. This impairs the function of the valves and further reduces the heart's ability to supply blood.

The assignee of this disclosure has developed a device that can be placed on an enlarged heart and fit snugly. One implementation of the assignee's device is characterized as a knit jacket device that is fit around a heart and then secured thereto through a variety of means. The jacket helps to constrain cardiac expansion beyond a predetermined limit. Examples of useable jackets are described in U.S. Pat. Nos. 5,702,343; 6,123,662; 6,241,654; 6,085,754; 6,230,714; 6,169,922; 6,155,972; 6,193,648; 6,293,906; 6,482,146; 6,425,856; 6,572,533; 6,564,094; and 6,416,459. Each of the foregoing patents is incorporated herein by reference.

To place a cardiac constraint jacket around a heart, internal access to the heart is necessary. It is desirable to avoid exposing the patient to trauma. In general, less invasive techniques are preferred to more invasive techniques. Improvements in accessing the heart and placing cardiac constraint devices are desirable.

SUMMARY

In accordance with principles of this disclosure, a method for applying a cardiac support device to a heart of a mammal includes surgically accessing a heart; providing a cardiac support device including a jacket; and positioning the jacket around at least a portion of the heart by applying a pulling force to the jacket.

Preferably, the step of positioning the jacket includes using a tool from a position superior to the heart to pull the jacket onto the heart.

In accordance with principles of this disclosure, a device for placing a cardiac support jacket onto a heart includes first and second tubular walls. The second tubular wall is oriented within the first tubular wall and against an internal surface of the first tubular wall. The second tubular wall includes a plurality of grooves and has an open interior volume constructed and arranged to hold a cardiac support jacket.

In accordance with principles of this disclosure, a device for placing a cardiac support jacket onto a heart includes a tubular wall having an open insertion end, an opposite end, and a plurality of lumens extending at least partially between the insertion end and the opposite end. In preferred implementations, the insertion end defines a plurality of notches, each notch preferably being along an internal surface of the tubular wall and in communication with a respective one of the lumens. An open interior volume of the tubular wall is constructed and arranged to hold a cardiac support jacket.

BRIEF DESCRIPTION OF THE DRAWINGS

FIG. 3 is a schematic, fragmented, cross-sectional view of one embodiment of a delivery device useable to place the cardiac support device of FIG. 1 onto a heart;

FIG. 4 is a cross-sectional view of the delivery device of FIG. 3 taken along the line 4—4 of FIG. 3;

DETAILED DESCRIPTION

Figure 1:
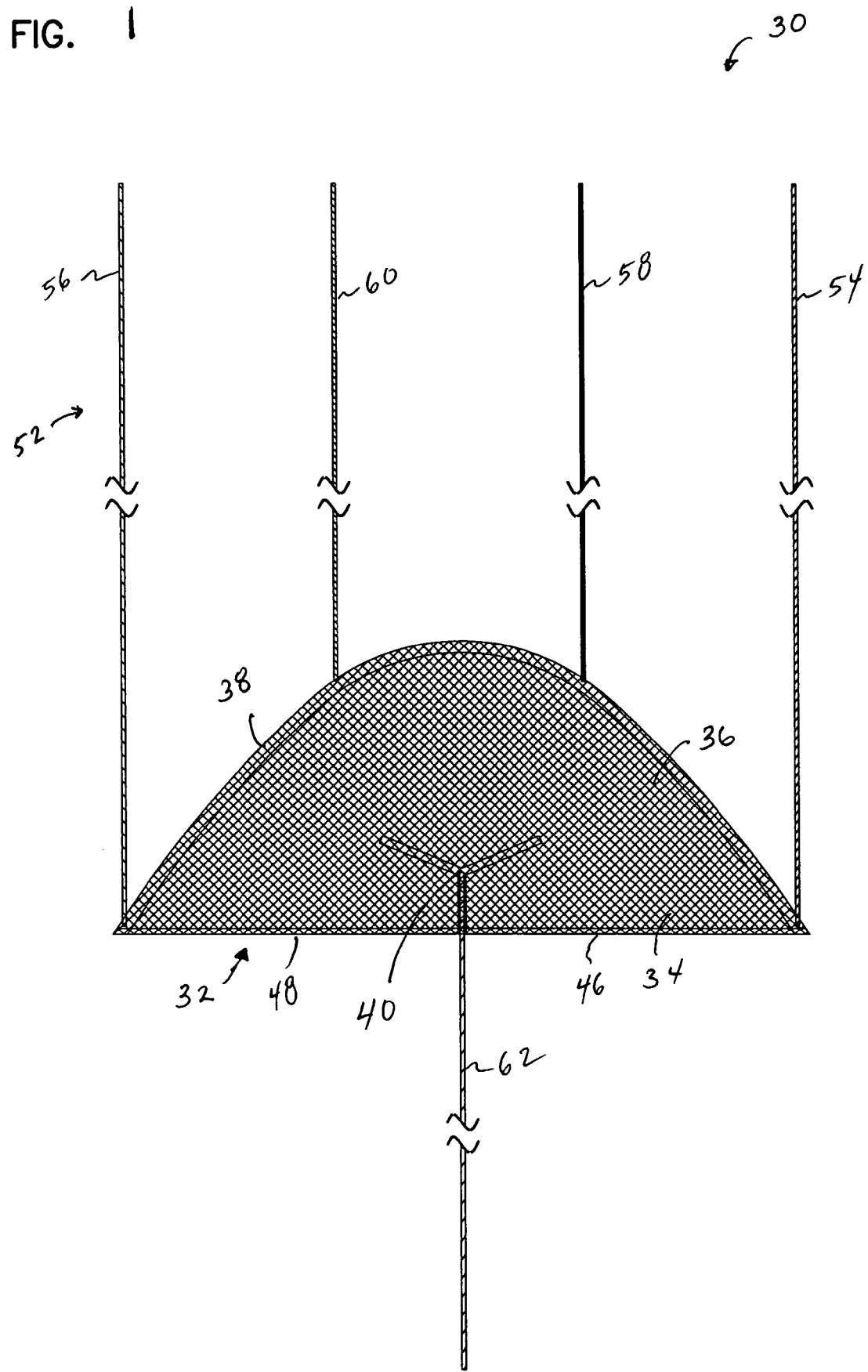
FIG. 1 is a schematic top plan view of a cardiac support device constructed in accordance with principles of this disclosure.
Figure 2:
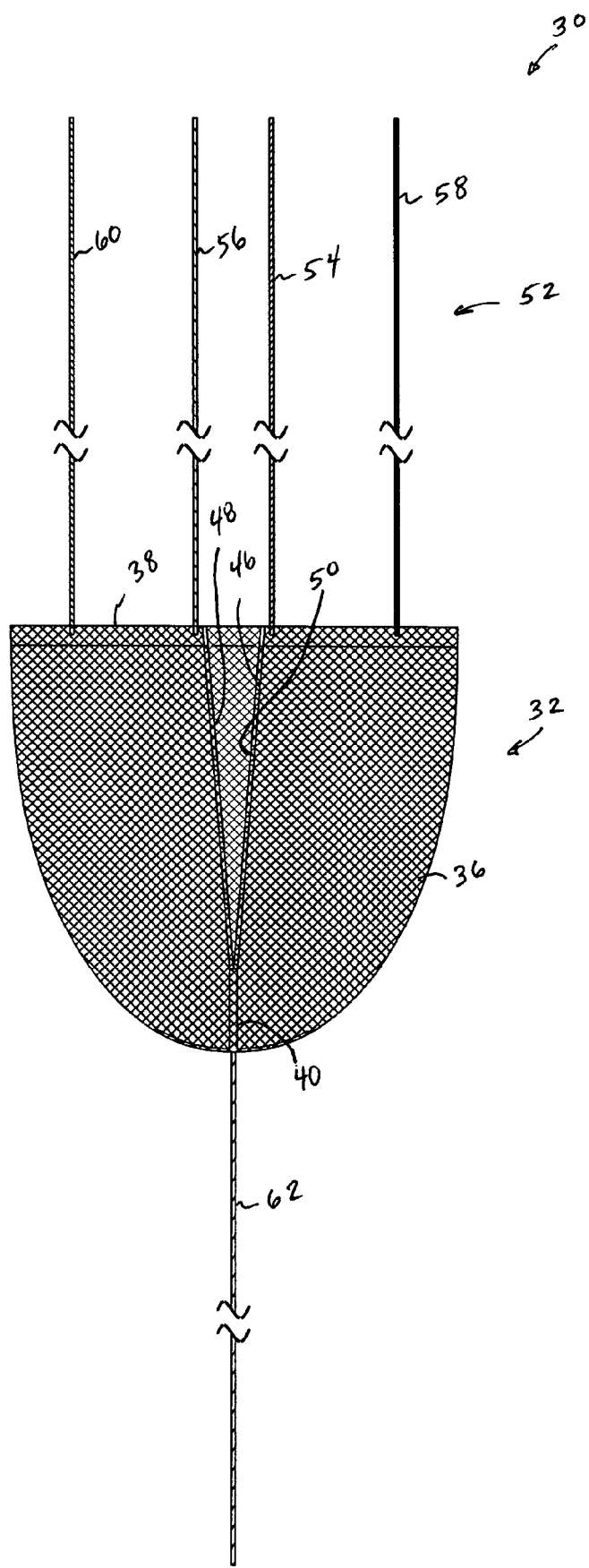
FIG. 2 is a schematic top plan view of the cardiac support device of FIG. 1 and folded over itself.

One embodiment of a cardiac support device useable with techniques described herein is shown generally in FIGS. 1 and 2 at 30. The cardiac support device 30, when operably placed onto the heart of a mammal, will limit the outward expansion of the heart wall during diastolic chamber filling beyond a predetermined size. The expansion constraint applied to the heart by the cardiac support device 30 is determined by the physician based upon, for example, cardiac output performance or cardiac volume. The cardiac support device 30 provides cardiac reinforcement during diastole.

Figure 15:
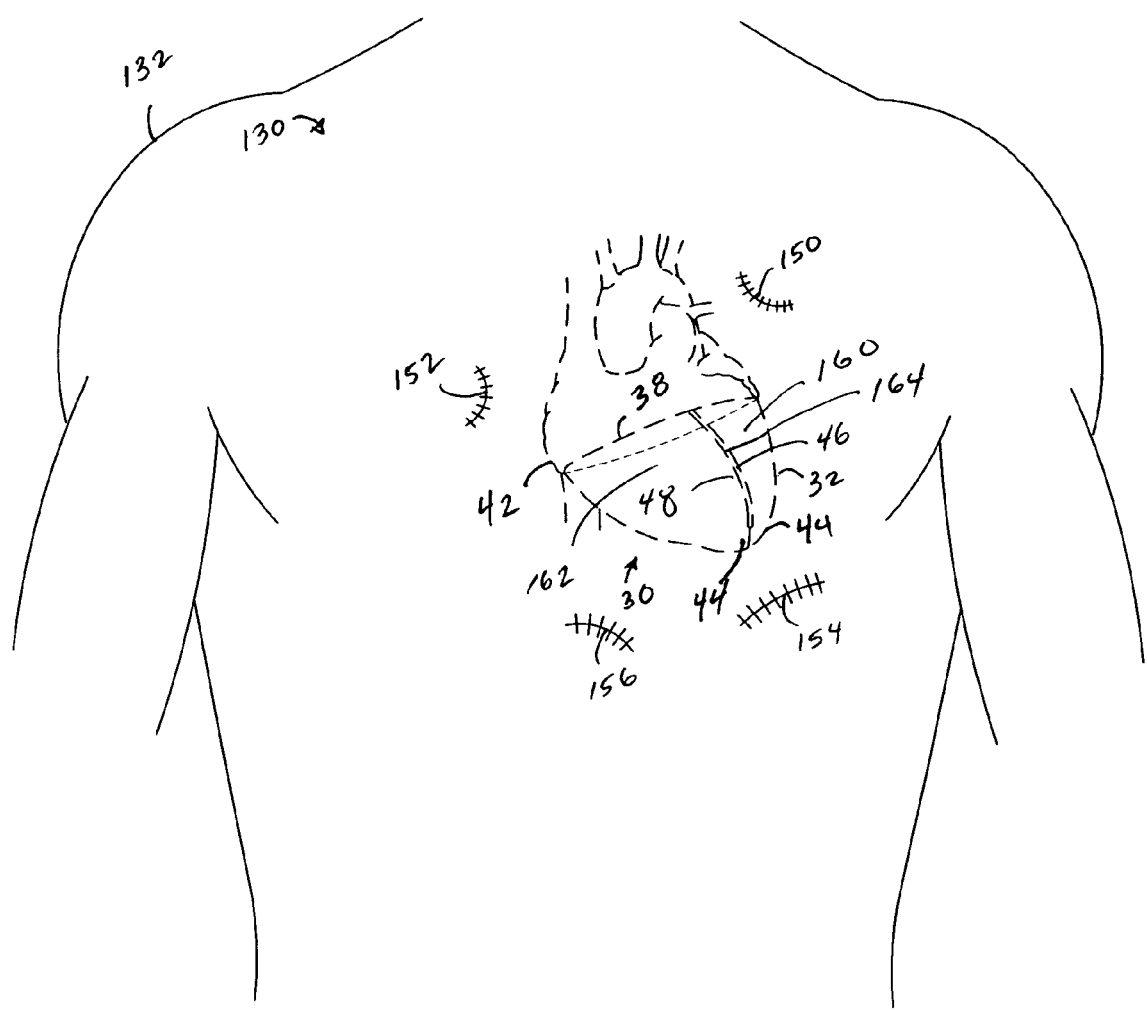
FIG. 15 is a schematic view showing the cardiac support device of FIG. 1 operably secured over the heart.

For purposes of the method of this disclosure and the apparatus or device used for the method, many types of cardiac support devices 30 are useable. The particular cardiac support device 30 depicted in FIG. 1 is a jacket 32. Preferred jackets 32 will be constructed of a biologically compatible material. In preferred implementations, the jacket 32 is a knitted construction 34. In the specific example shown, the knitted construction 34 includes a continuous, flexible mesh net 36 having a base edge 38 and an opposite apex 40. It should be noted that the jacket 32 depicted in FIG. 1 is shown before placement onto a heart and in a flattened position. FIG. 2 schematically shows the jacket 32 as it would appear around a heart before being tightened and seamed, but the heart is not depicted in FIG. 2. FIG. 15 shows the jacket 32 wrapped around a heart 42. The base edge 38 can be seen forming a peripheral edge opposite from the apex 40, which is located in snugging engagement with the heart apex 44.

Still in reference to FIG. 1, the particular jacket 32 depicted in the drawings also includes a first lateral edge 46 and a second lateral edge 48 extending from the base edge 38. When wrapped around the heart 42, the jacket 32 is shaped such that the first lateral edge 46 and second lateral edge 48 are adjacent and opposing each other to define an open slot 50 (FIG. 2). In the cardiac support device 30 shown, the slot 50 generally extends from the base edge 38 and terminates at the apex 40.

In accordance with principles of this disclosure, the cardiac support device 30 further includes positioning strands, sutures, tethers, or strings in a system 52. The string system 52 can be grasped with appropriate tools in order to exert a pulling force onto the jacket 32 and manipulate the jacket 32 into operable position over the heart 42.

In the particular arrangement shown, the positioning string system 52 includes a first anterior strand 54 secured to the base edge 38 adjacent to the first lateral edge 46. The string system 52 further includes a second anterior strand 56 secured to the base edge 38 adjacent to the second lateral edge 48. The string system 52 also includes a first posterior strand 58 secured to the base edge 38 and positioned closer to the first anterior strand 54 than to the second anterior strand 56. Further, the string system 52 preferably includes a second posterior strand 60 secured to the base edge 38 and positioned closer to the second anterior strand 56 than to the first anterior strand 54. As can be seen in FIG. 1, in the particular arrangement illustrated, when viewing the jacket 32 as pressed flat, the first anterior strand 54 and second anterior strand 56 form the outside edges of the string system 52, while the first posterior strand 58 and second posterior strand 60 are between the anterior strands 54 and 56. It should be appreciated that the illustrated embodiment shows the string system 52 as being secured to the base edge 38. In other embodiments, the particular strands of the string system 52 can be secured to other portions of the jacket 32. The configuration shown was found to be convenient. In other embodiments, the particular strands of the string system 52 can be secured to the jacket 32 with loops, permitting convenient, quick, and easy removability from the jacket 32 by clipping.

In addition, in the particular embodiment shown in FIG. 1, in addition to the string system 52, there is an apex strand 62 secured to the apex 40. Each of the strands in the string system 52 and the apex strand 62 is constructed of a biocompatible material and is strong enough to sustain a pulling force against resistance offered by internal body tissue. Each of the strands of the string system 52 and the apex strand 62 is sufficiently long enough to allow for manipulation of tools in order to position the jacket 32 over the heart 42. In typical, useable embodiments, each of the strands of the string system 52 and the apex strand 62 will be at least two inches, and not greater than 50 inches.

In accordance with principles of this disclosure, a method and apparatus are provided for applying the cardiac support device 30 to the heart 42. In preferred techniques, the method used is less invasive than certain prior art methods for treating heart disease. Some of these prior art methods include a full sternotomy, in which the sternum is split lengthwise, a rib spreader is used, and the heart is exposed.

In reference now to FIG. 3, one embodiment of a device for positioning the cardiac support device 30 is shown in schematic, fragmented, partially cross-sectional view in FIG. 3 generally at 70. While many different implementations are possible, in the particular embodiment shown in FIGS. 3 and 4, the device 70 includes a first tube 72. The tube 72 is defined by a first tubular wall 74 having an open, insertion end 76, an opposite end 78, and an internal surface 80 on the tubular wall 74. The end 78 can have a variety of geometries. In the example shown, the end 78 is illustrated as being closed with an end cap 82 that plugs the end 78. The end cap 82 preferably defines an aperture to allow for the passage of the apex strand 62, when the cardiac support device 30 is loaded within the device 70 for placement over the heart 42.

In the particular one shown, the end cap 82 further defines an aperture or port 83 usable for receiving a syringe in use. A syringe can be mounted in communication with the port 83 to permit the addition of selected fluids, such as saline, into the device 70. The particular end cap 82 illustrated in FIG. 3 also includes a strand-holding groove 85 to accommodate holding the apex strand 62 that is secured to the jacket 32. As can be seen in FIG. 3, the apex strand 62 can be wrapped around the end cap 82 and held within the strand-holding groove 85. The end cap 82 can also have a notch or holding slot 87 for holding or parking the apex strand 62 in place. The arrangement of the strand-holding groove 85 and holding slot 87 helps to hold the apex strand 62 in place and anchor the apex strand 62 to avoid unintentionally yanking of the jacket 32 from the device 70.

The insertion end 76 is illustrated as defining an oblique opening 84, when compared to the tubular wall 74. The oblique opening 84 defines a forward insertion region 86 and is shaped generally to allow for an easy, smooth insertion of the device 70 through tissue. The insertion end 76, in the one shown, can also be described as wedge-shaped. The wedge-shape allows the device 70 to be easily slid under the posterior side of the heart 42.

In general, in the particular embodiment illustrated, the first tube 72 is cylindrical, such that it forms a circular cross-section. This can be seen in the cross-section shown in FIG. 4. This cross-section is preferably uniform through most of the device 70 (that is, at least 75% of the length, typically at least 90% of the length). In the embodiment illustrated, the insertion end 76 of the first tube 72 deviates from the circular cross-section to define an obround, oval, racetrack-shaped, or elliptical cross-section. In FIG. 3, it can be seen how the tubular wall 74 deviates from being generally parallel to a central longitudinal axis 88 at the insertion end 76 and adjacent to the oblique opening 84. This particular geometry is helpful in inserting the device 70 through tissue and under the posterior of the heart 42. The insertion end 76 includes an elongate face 89 culminating an insertion region 86 at an outer most tip 86a. Elongate face 89 is longer than the portion 91 of the insertion end 76. As such, the oblique opening 84 is defined by the end of portion 91 and the end of elongate face 89.

The insertion end 76 preferably defines holding structure 90 for temporarily and selectively securing the string system 52 to the device 70. Many different types of holding structures 90 are useable. One particular type of holding structure 90 useable are a plurality of slots 92. The slots 92 shown have these features: in FIG. 3, there are the same number of slots 92 as there are strands in the string system 52 (although, in other embodiments, there can be more). Each slot is defined as a cut or notch 94 in the tubular wall 74 at the insertion end 76 and along the oblique opening 84. In the embodiment shown in FIG. 3, there are four notches 94, depicted as slits 96, 97, 98, and 99. In the embodiment shown in FIG. 3, the holding structure 90 is oriented in the elongate face 89. The slits 96, 97, 98, and 99 are located on the elongate face 89 so that surgical tools can be used to grasp strings 52. When configured in this fashion, the elongate face 89 functions as a backboard for helping manipulation of the strings 52 with surgical tools, such as a forceps.

In preferred implementations, the slit 96 holds the first anterior strand 54; the slit 97 holds the first posterior strand 58; the slit 98 holds the second posterior stand 60; and the slit 99 holds the second anterior strand 56. Of course, other arrangements of notches 94 and strands are contemplated and useable.

Still in reference to FIGS. 3 and 4, the device 70 further includes a second tube 102. The second tube 102 includes a second tubular wall 104 including a first end 106, a second end 108, an external surface 110 on the second tubular wall 104, and an internal surface 112 on the second tubular wall 104.

In FIG. 3, it can be seen how the second tubular wall 104 is oriented within the first tubular wall 72 such that the first tubular wall 72 circumscribes the second tubular wall 104. In the particular embodiment illustrated, the second tubular wall 104 is oriented within the first tubular wall 72 such that the external surface 110 of the second tubular wall 104 is positioned snugly against the internal surface 80 of the first tubular wall 72. In the embodiment shown in FIG. 3, the second tubular wall 104 has an overall length that is less than the first tubular wall 72. Thus, it can be seen that the second tubular wall 104 ends at first end 106 and does not extend into the insertion end 76 of the first tube 72.

The second tube 102, in the embodiment shown, further includes a plurality of grooves 114 extending at least partially between the first end 106 and second end 108. In preferred embodiments, the plurality of grooves 114 extend completely between the first end 106 and second end 108. There can be any number of grooves 114. In the preferred embodiment illustrated, there is an equal number of grooves 114 as there are strands in the string system 52. In FIG. 4, grooves 114 are shown as four individual, and equally spaced-apart channels 116, 117, 118, and 119. The channels 116–119 form open volumes 122 between the internal surface 80 of the first tube 72 and the second tube 102. In the preferred embodiment illustrated, each channel 116–119 holds one of the strands of the string system 52, when the cardiac support device 30 is loaded within the device 70 for placement onto heart 42. The strands in the string system 52 can be folded multiple times in order to fit within the appropriate channel 116–119.

The second tubular wall 104 defines an open interior volume 124 that is constructed and arranged to hold the cardiac support device 30. As described above, one useable cardiac support device 30 includes jacket 32 constructed of mesh net 36. As such, the jacket 32 is collapsible and can fit into the open interior volume 124.

When the device 70 is loaded with the cardiac support device 30 for placement of the jacket 32 onto the heart 42, the apex strand 62 extends through an opening in the end cap 82, and the jacket 32 is collapsed into a bundle 126. Each of the strands of the string system 52 is directed out through the first end 106 of the second tube 102. Each strand 54, 56, 58, and 60 is individually inserted into a respective one of the channels 116, 117, 118, 119. The channels 116–119 function, for among other reasons, to hold the slack of each of the strands 54, 56, 58, 60 and help to prevent tangling of the strands in the device 70. Each of the strands 54, 56, 58, 60 extends from the respective channel 116–119 and is held by a respective slit 96, 97, 98, 99. The device 70 is then ready to be used to operably place the jacket 32 onto the heart 42.

Figure 16:
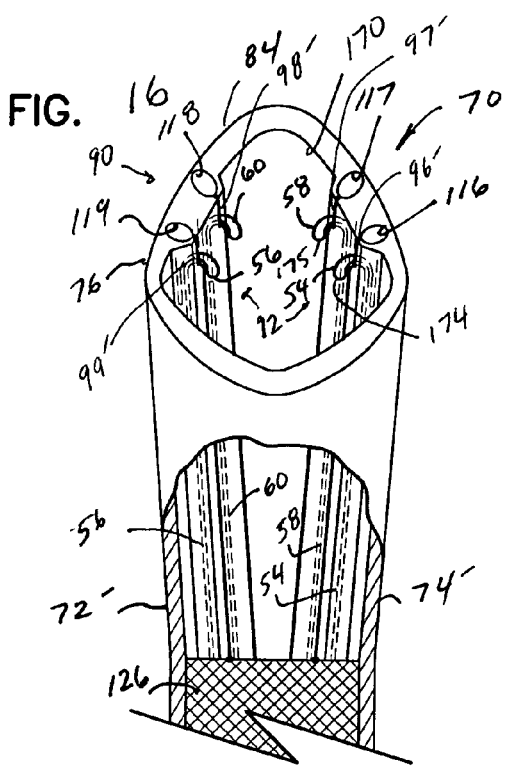
FIG. 16 is a schematic, fragmented, cross-sectional view of another embodiment of a delivery device usable to place the cardiac support device of FIG. 1 onto a heart.
Figure 18:
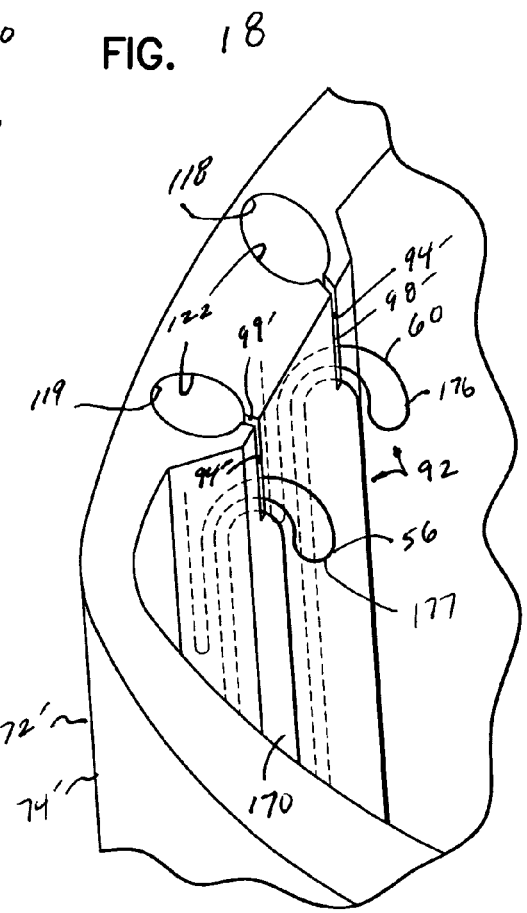
FIG. 18 is an enlarged, fragmented view of a portion of the delivery device of FIG. 16.
Figure 17:
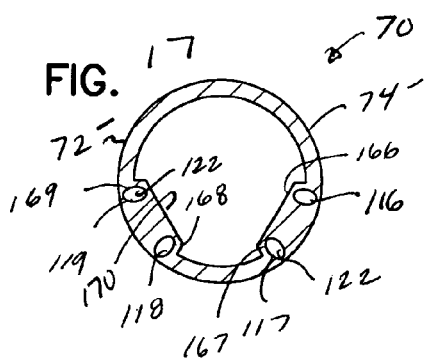
FIG. 17 is a cross-sectional view of the delivery device of FIG. 16, taken along the line 17—17 of FIG. 16.

In reference now to FIGS. 16–18, an alternate embodiment of the device 70 is illustrated. Device 70, shown in FIGS. 16–18, differs from the embodiment of FIGS. 3 and 4 in that there is a single tube 72'. Tube 72' differs from tube 72 in FIG. 3 in that it includes channels 116–119 molded there within. The tube 72' can be conveniently manufactured by extrusion, with a tubular wall 74' extruded along with the channels 116–119. As with the embodiment of FIGS. 3 and 4, the channels 116–119 in FIGS. 16–18 define open volumes 122 for accommodating one of the strands of the string system 52. In the example embodiment illustrated, each of the channels 116–119 extends completely between the oblique opening 84 and the opposite end 78. In FIG. 17, it can be seen how each of the channels 116–119 is completely enclosed, to form closed tubes or lumens 166, 167, 168, 169 having opposite open ends at oblique opening 84 and opposite end 78. The strings in the string system 52 are shown positioned within the open volumes 122 in a respective channel 116–119. The strings in the string system can be folded multiple times in order to fit within the appropriate channel 116–119.

The insertion end 76 of the tube 72' also defines holding structure 90 for temporarily and selectively securing the string system 52 to the device 70. In the FIG. 3 embodiment, the holding structure 90 includes slots 92 formed as cut or notch 94 in the wall 74 at the insertion end and along the oblique opening 84. In the embodiment of FIG. 16, the holding structure 90 is also in the form of slots 92, but is defined as cut or notch 94' along the inside surface 170 of the tubular wall 74'. Each cut or notch 94' extends from the open end at the oblique opening 84 partially down the inside surface 170 of each lumen 166–169 and in communication with the open volume 122 of each of the channels 116–119. Each of the strings of the string system 52 is held within a respective notch 94'. In the embodiment shown in FIG. 16, there are four notches 94', depicted as slits 96', 97', 98', and 99'.

In the implementation illustrated in FIG. 16, the slit 96' holds the first anterior strand 54; the slit 97' holds the first posterior strand 58; the slit 98' holds the second posterior strand 60; and the slit 99' holds the second anterior strand 56. FIG. 18 illustrates one example technique for holding the strands of the string system 52 in their respective channels 116–119. Each strand is parked within its respective slit 96'–99' and looped back over itself to form a grasping loop 174, 175, 176, 177. Each of the strands of the string system 52, in the embodiment illustrated, is shown to be oriented within device 70 to have a respective grasping loop 174–177. The grasping loops 174–177 can be grasped and manipulated by surgical tools, such as forceps and hooks in order to deploy the jacket 32 from the device 70 and onto the heart 42. This is described further below.

The tube 72 can be constructed of materials that allow for less trauma on the body, such as a flexible low density polyethylene (LDPE). The flexibility of the material of the tube 72 is preferably greater than the flexibility of a typical, normal human rib.

Figure 5:
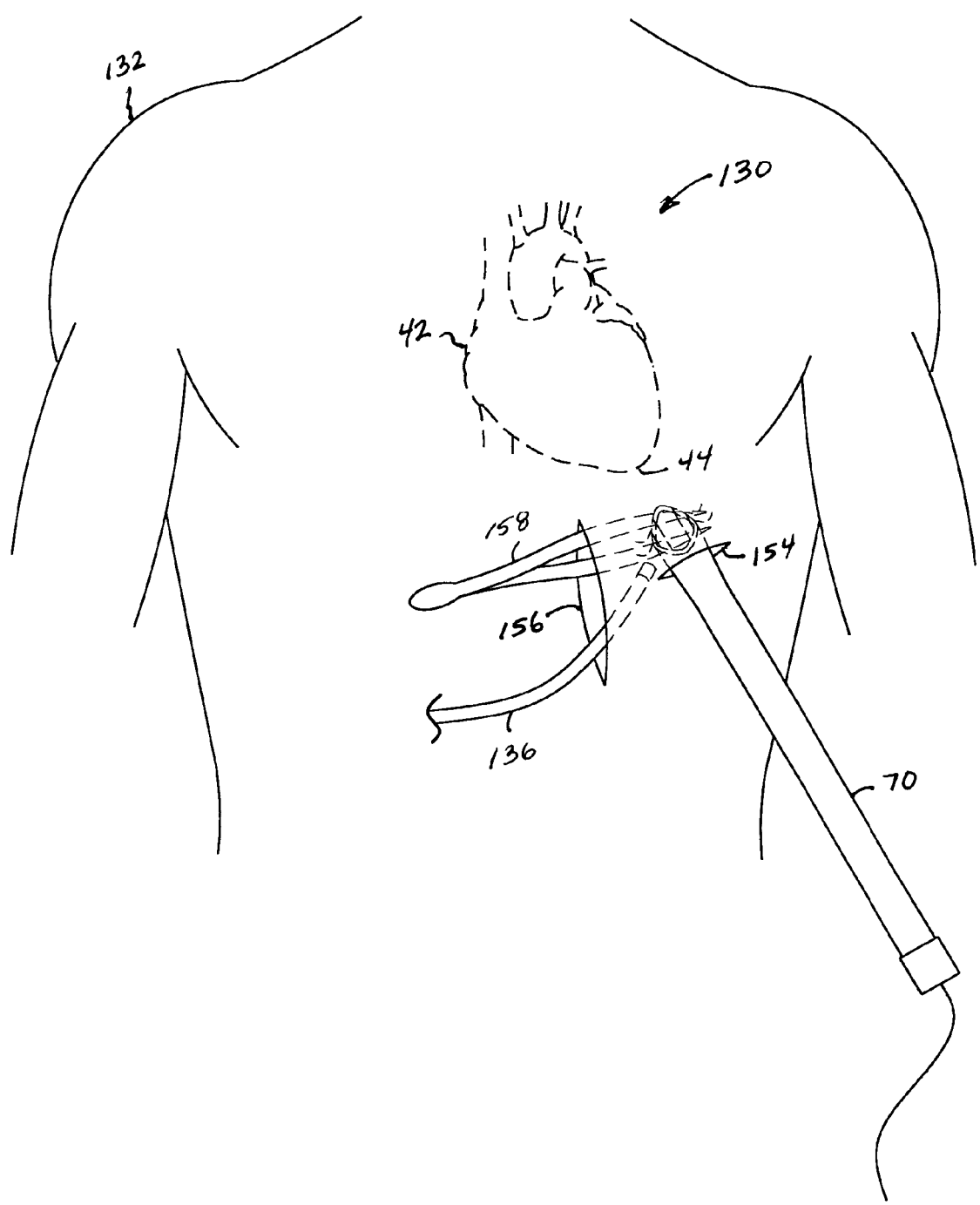
FIG. 5 is a schematic view showing one step of placement of the cardiac support device of FIG. 1 onto a heart.

In reference now to FIGS. 5–14, a method in accordance with principles of this disclosure for applying the cardiac support device 30 is illustrated schematically. FIG. 5 shows in general a thoracic region 130 of a mammal, e.g. a human 132, having heart 42. The heart 42 is shown in dashed lines to indicate that it is below the exterior surface of the thoracic region 130.

In FIG. 5, an initial step is illustrated and includes inserting a viewing device, such as an endoscope 136 into the thoracic region 130 in a position below, or inferior to, the heart 42. The endoscope 136 helps the surgeon to be able to visually observe subsequent steps in the method to help properly place the jacket 32 over the heart 42. Of course, the endoscope 136 can be other means that allow for visualization. The endoscope 136 can be positioned by performing a subxyphoid incision 156 at the midline, an intercostal incision, or a subcostal incision.

The device 70, properly loaded with the cardiac support device 30 therein, is then inserted into the thorax 130. In the example shown, the device 70 is inserted into the left thoracic region through an intercostal incision or subcostal incision.

In general, the heart 42 is surgically accessed, the cardiac support device 30 is provided, and the jacket 32 is positioned around at least a portion of the heart 42 by applying a pulling force to the jacket 32. In one example, the step of positioning includes pulling the jacket 32 from a position superior to the heart 42. In some implementations, the jacket 32 is pulled over the heart 42 in a single step. In other implementations, the jacket 32 is positioned over and around the heart 42 by pulling in multiple steps. In one example, the jacket 32 is positioned by pulling in a first direction a first portion of the jacket 32 and then pulling in a second direction, a second portion of the jacket 32 onto the heart 42.

A surgical tool, such as a forceps, grasper, or pick-ups 158 can be used to assist in deploying the jacket 32 from the device 70. Examples for how the pick-ups 158 is used in connection with the device 70 are discussed further below.

Figure 6:
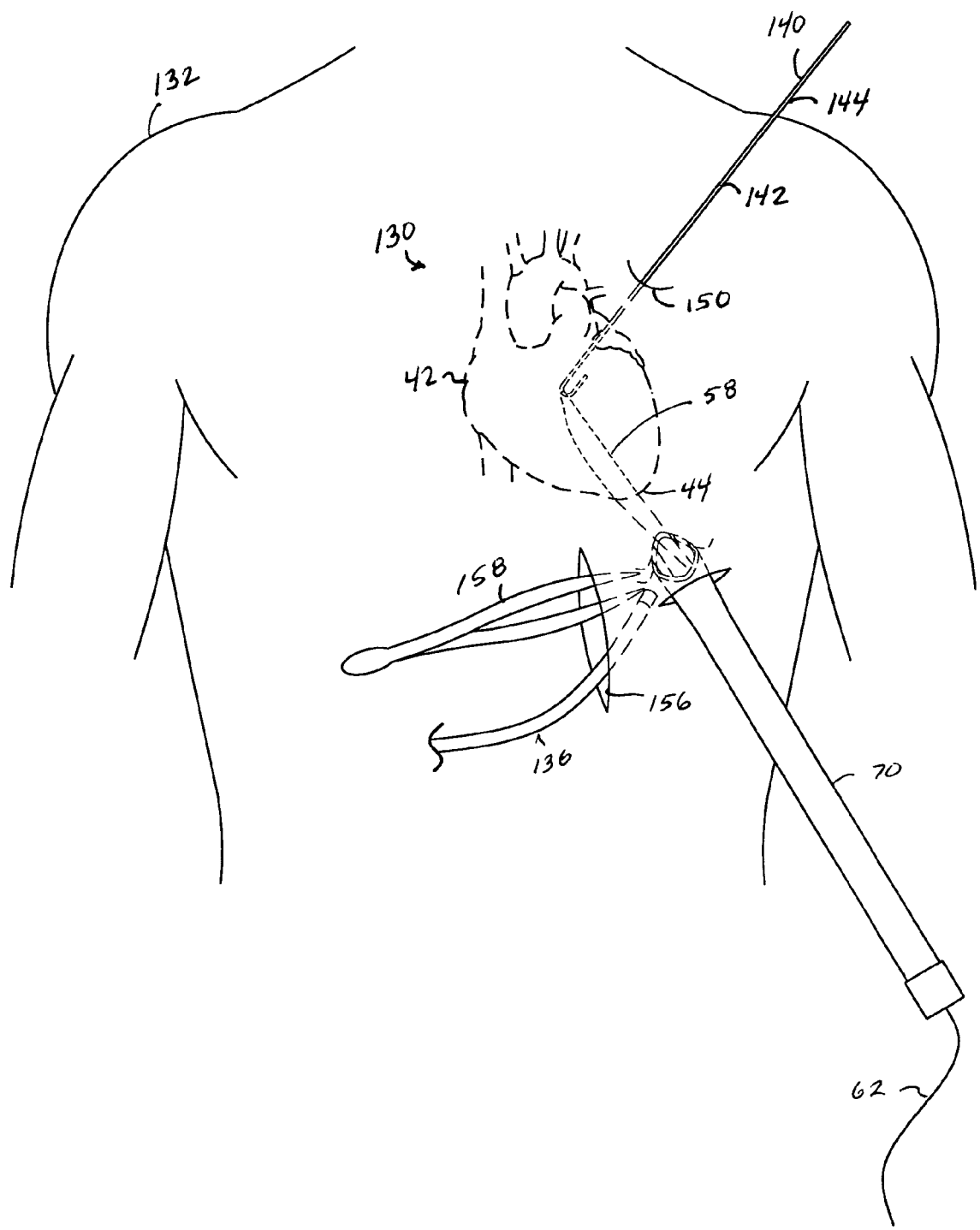
FIGS. 6–14 show additional steps in placement of the cardiac support device of FIG. 1 onto the heart.

In FIG. 6, another step of an example implementation is illustrated. In FIG. 6, a tool 140 is used to apply the pulling force to the jacket 32 in order to position the jacket 32 onto the heart 42. Many types of tools 140 are useable. One useable tool 140 is a snare 142. The snare 142 shown generally has an elongate handle 144 for manipulation by the surgeon and an end hook 146 for grasping and applying the pulling force to the jacket 32. FIG. 6 illustrates a step of surgically inserting the tool 140 into the thorax 130 in a position superior to the delivery device 70. In certain preferred implementations, the tool 140 is surgically inserted through an incision 150 in the second intercostal region. In FIG. 6, specifically, the tool 140 is inserted into the left second intercostal region. The tool 140 can be inserted in other areas.

Figure 7:
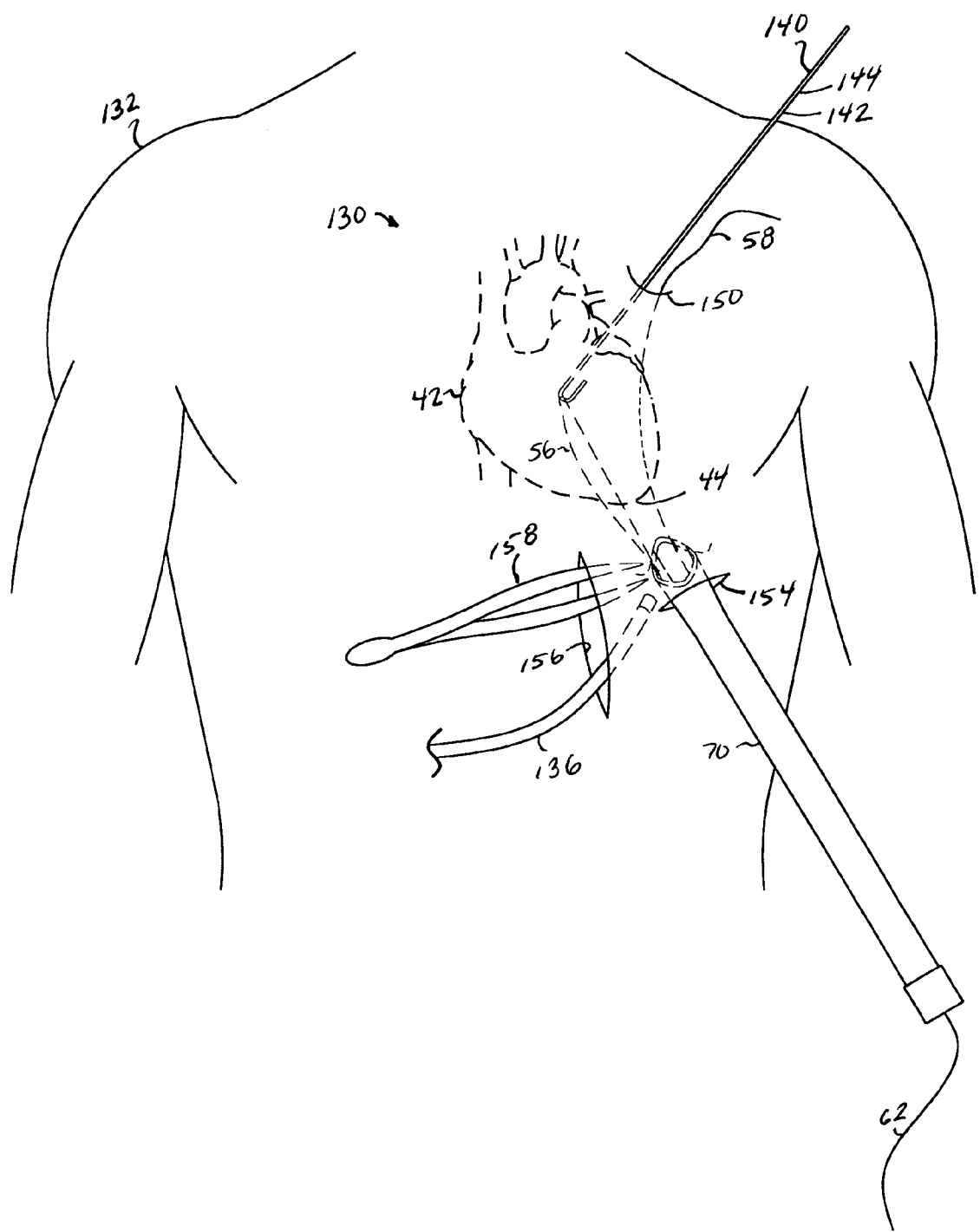
Figure 8:
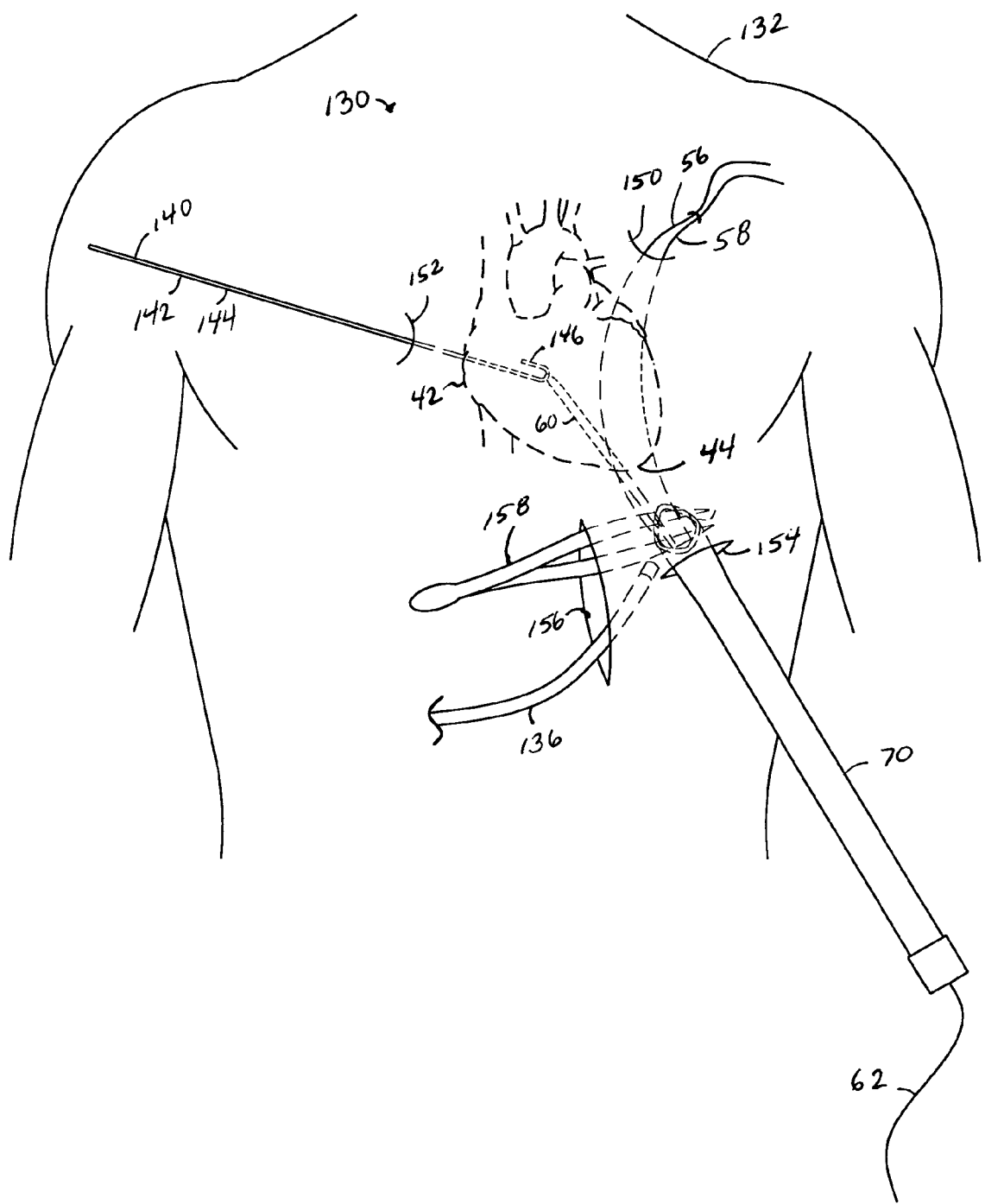
Figure 9:
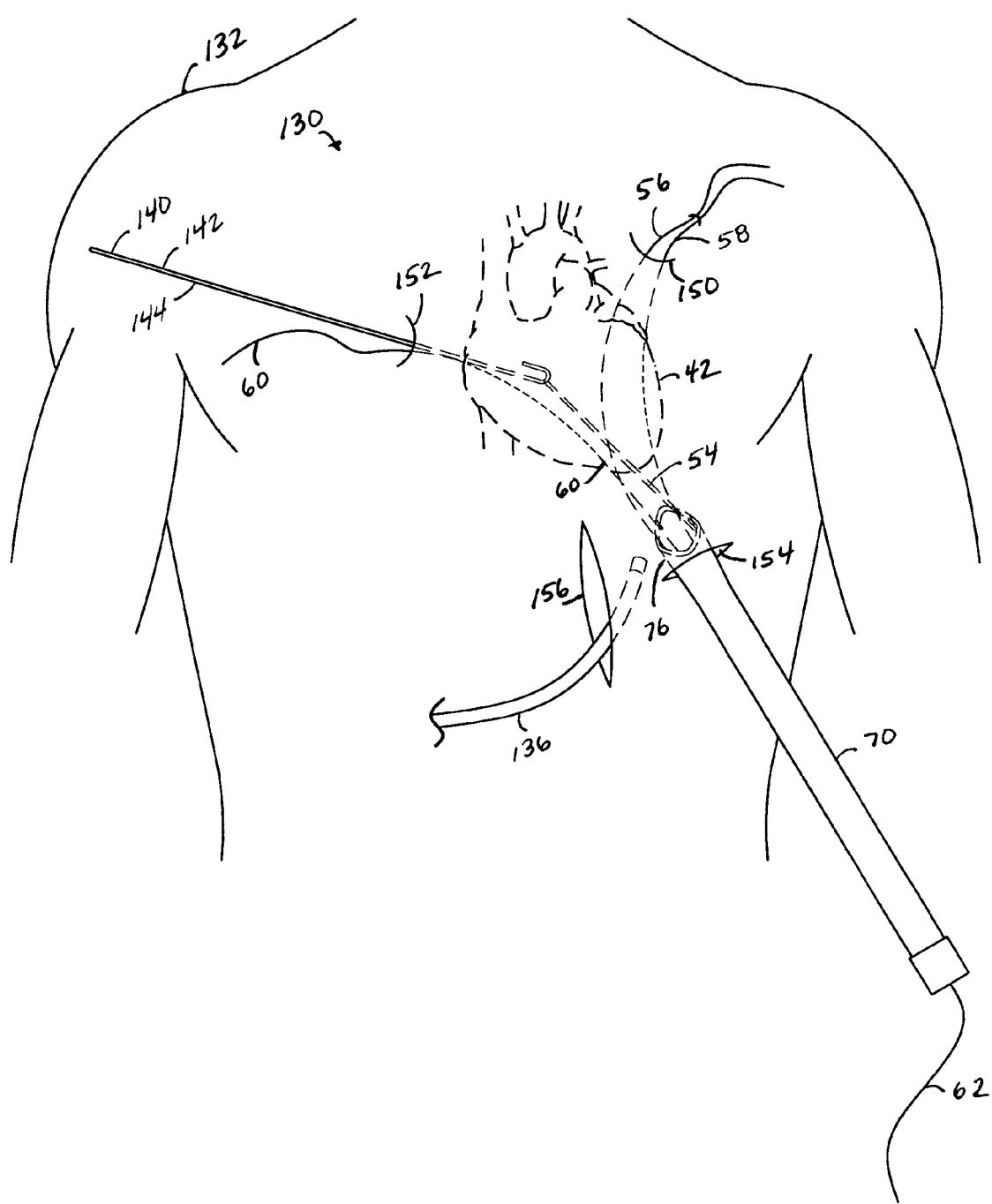

In general, the tool 140 can be used to pull in a first direction a portion of the jacket 32 onto the heart, and then the tool 140 can be used to pull in a second direction a second portion of the jacket 32 onto the heart 42. FIGS. 6 and 7 show the tool 140 being used to pull in a first direction at least a portion of the jacket 32 onto the heart 42, while FIGS. 8 and 9 show the tool 140 being used to pull in a second direction a second portion of the jacket 32 onto the heart 42. The tool 140 shown in FIGS. 6 and 7 can be the same or a different tool 140 shown in FIGS. 8 and 9. In certain, example methods, the tool 140 is used to grasp strands in the string system 52 in order to apply the pulling force to the jacket 32.

Still in reference to FIG. 6, one step in an example method is shown including, first, from a first position superior to the heart 42, pulling the first posterior strand 58. The pick-ups 158 are illustrated as being inserted through the incision 156. In the example shown, the pick-ups 156 grasp the first posterior strand 58 from the holding structure 90, e.g., either slit 96 or slit 96'. Using the FIG. 16 embodiment, the pick-ups 158 grasp the loop 175. Next, the first posterior strand 58 is grasped by the hook 146 of the tool 140 by inserting the snare 142 through the left second intercostal region, which is superior to the heart 42 and superior to the inserted device 70. The first posterior strand 58 is pulled from the slit 96, 96' to pass under the heart 42 and pulled out of the thorax 130 through the incision 150. FIG. 7 shows the first posterior strand 58 under the heart 42 and resting externally.

In the particular method illustrated, after the first posterior strand 58 is pulled from the device 70, to pass below the heart 42, and pulled outside of the body through the incision 150, the snare 142 is used to pull the second anterior strand 56 from a position superior to the heart 42. The second anterior strand 56 is initially pulled from the device 70 with pick-ups 158 and handed-off to the snare 142. The snare 142 pulls the second anterior strand 156 above or over the heart 42 and through the incision 150 to a position resting outside of the body. This is shown in FIG. 8.

In FIG. 8, the first posterior strand 58 and second anterior strand 56 are shown pulled from the device 70 and across the heart 42. First posterior strand 58 is shown pulled under the heart 42, while second anterior strand 56 is shown pulled over the heart 42. Each of the strands 56, 58 is pulled through the incision 150 and can be temporarily secured to the external portion of the body.

Still in reference to FIG. 8, next, in the particular example method illustrated, the tool 140, which may be the same as shown in FIGS. 6 and 7 or may be different, is inserted through an incision 152 in the right intercostal region to a position superior to the heart 42 and superior to the device 70. Again, the tool 140 can be snare 142. From this second position, superior to the heart 42, and lateral to the first position (incision 150), the step of pulling the second posterior strand 60 is conducted. In particular, the second posterior strand 60 is grasped with the hook 146 on the snare 142 and pulled under the heart 42 and through incision 152. FIG. 9 shows the second posterior strand 60 extending from the device 70, under the heart 42, and out through the incision 152. The pick-ups 158 are shown in the illustrated embodiment as pulling the strand 60 from slit 98, 98' to pass or hand-off to the hook 146.

Figure 10:
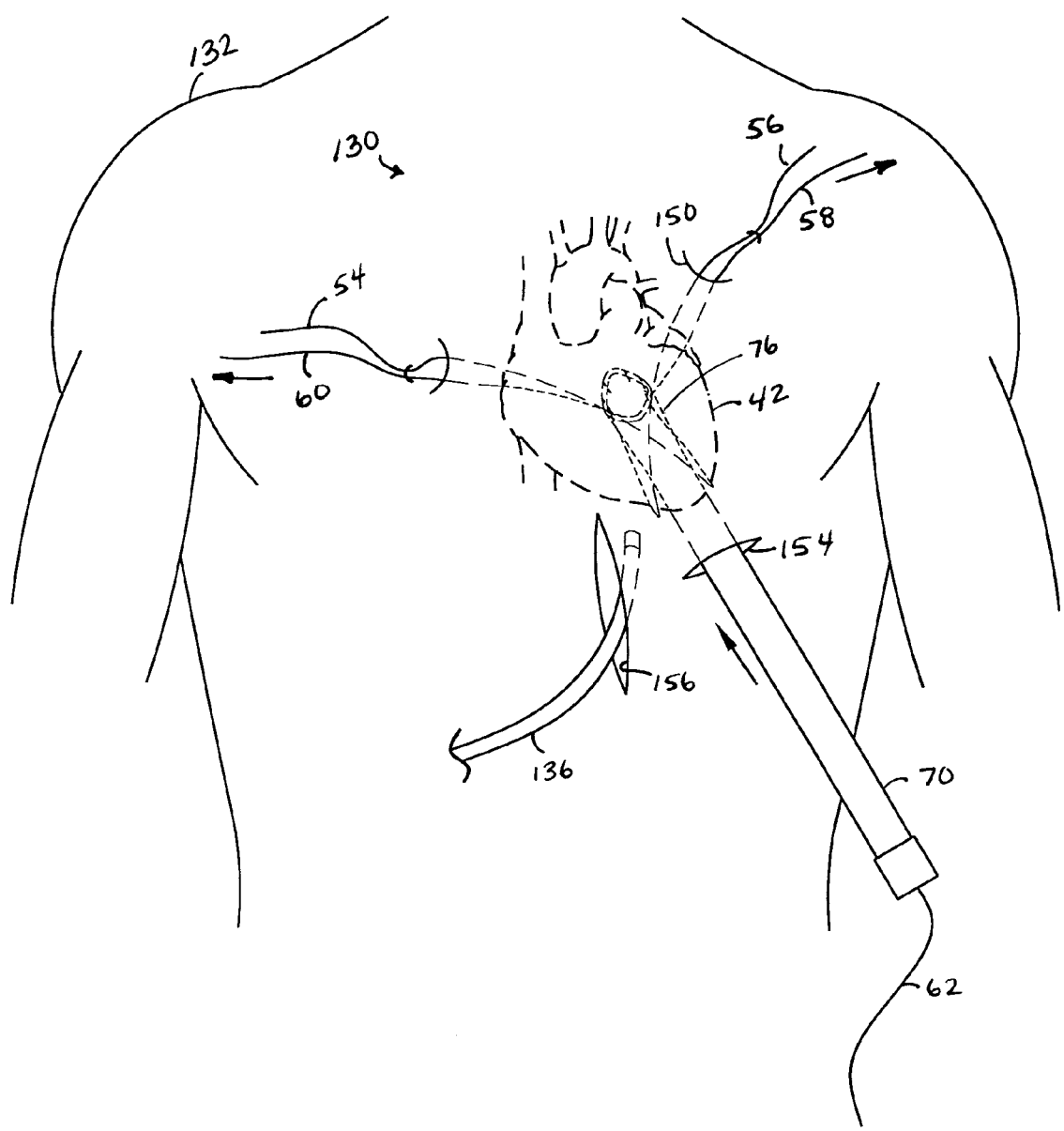

In FIG. 9, the next step in the example method is illustrated and includes pulling the first anterior strand 54 over the heart 42. In particular, the first anterior strand 54 is grasped with the hook 146 from the pick-ups 158 (shown in FIG. 8 are accessing strand 54) and pulled over the heart 42 and out of the body through the incision 152. FIG. 10 shows the first anterior strand 54 extending from the body through the incision 152. FIG. 10 shows the result after each of the strands in the string system 52 is initially pulled from the device 70 to positions superior to the device 70 and to the heart 42.

In reference now to FIG. 10, after the step of pulling the first posterior strand 58, second anterior strand 56, second posterior strand 60, and first anterior strand 54, the delivery device 70 is advanced into the thorax 130 to a position under the heart 42. In FIG. 10, it can be seen how the device 70 is grasped outside of the body and pushed through the incision 154 through the tissue under the heart 42. In some implementations, the device 70 is advanced into the thorax 130 until the insertion end 76 is just under the AV groove of the heart 42. After the delivery device 70 is advanced under the heart, the first posterior strand 58, the second posterior strand 60, and the apex strand 62 are pulled. In particular, the second posterior strand 60 is pulled in a direction toward the right side of the body, the first posterior strand 58 is pulled in a direction toward the left side of the body, and the apex strand 62 is pulled against the forces exerted by the first posterior strand 58 and second posterior strand 60.

Figure 11:
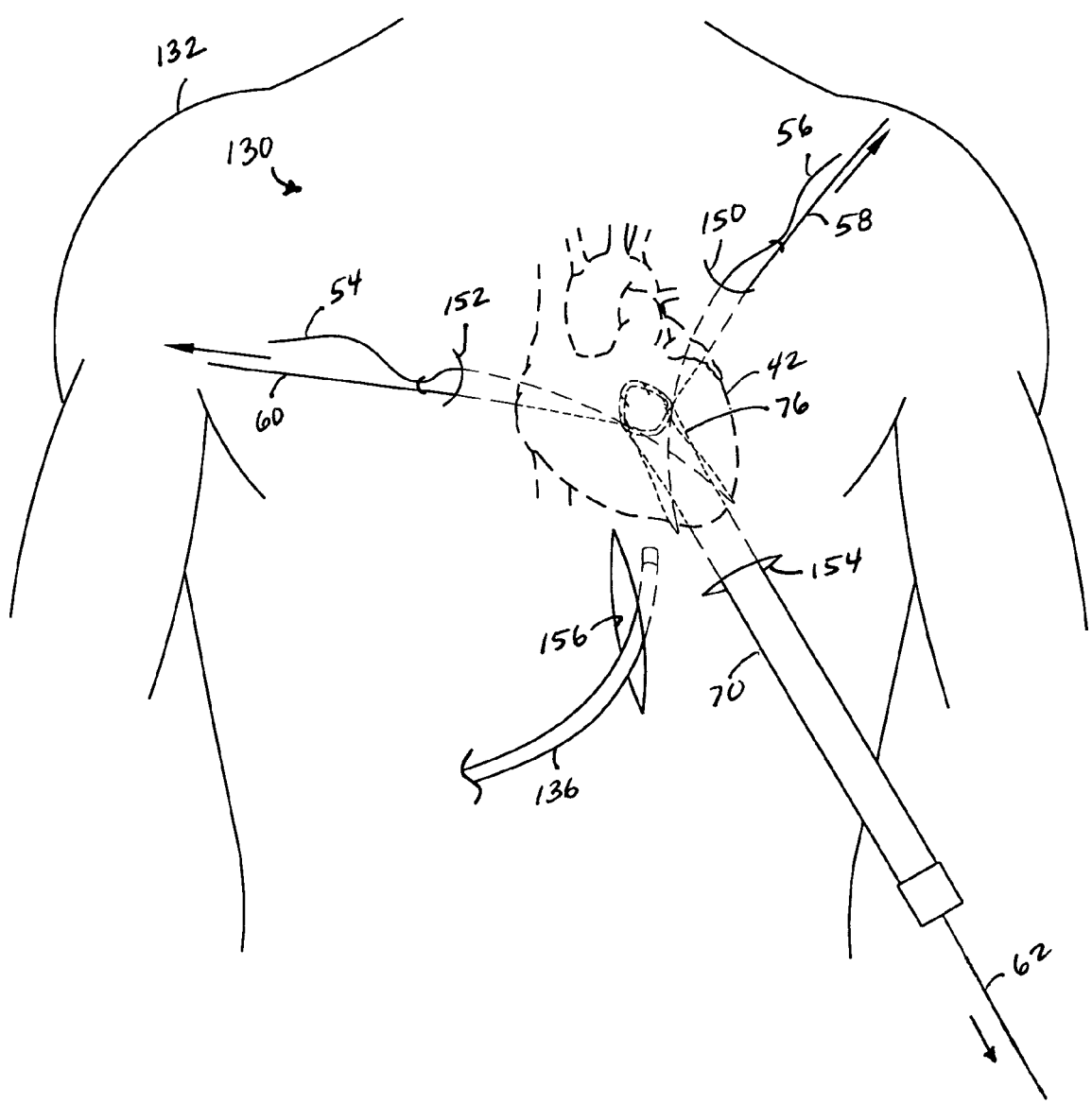

Next, and as shown in FIG. 11, the device 70 is pulled from outside of the thorax 130 and from the body through the incision 154. The apex strand 62 can be secured, temporarily, to the body by clamping, for example. Because of the pulling force of the first posterior strand 58 and second posterior strand 60 against the pulling force of the apex strand 62, the jacket 32 is transformed from the bundle 126 into a triangular configuration 127.

Figure 12:
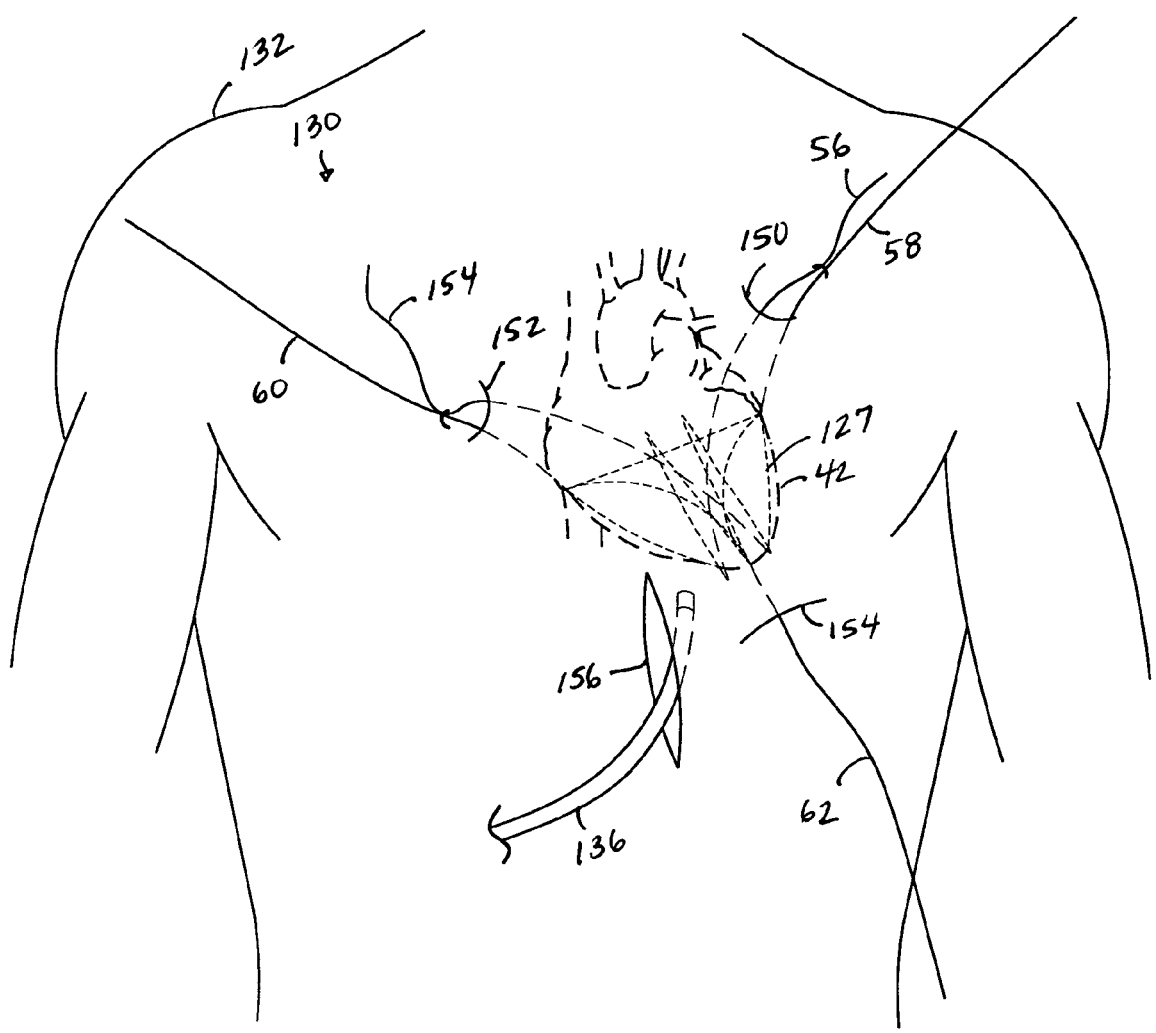
Figure 13:
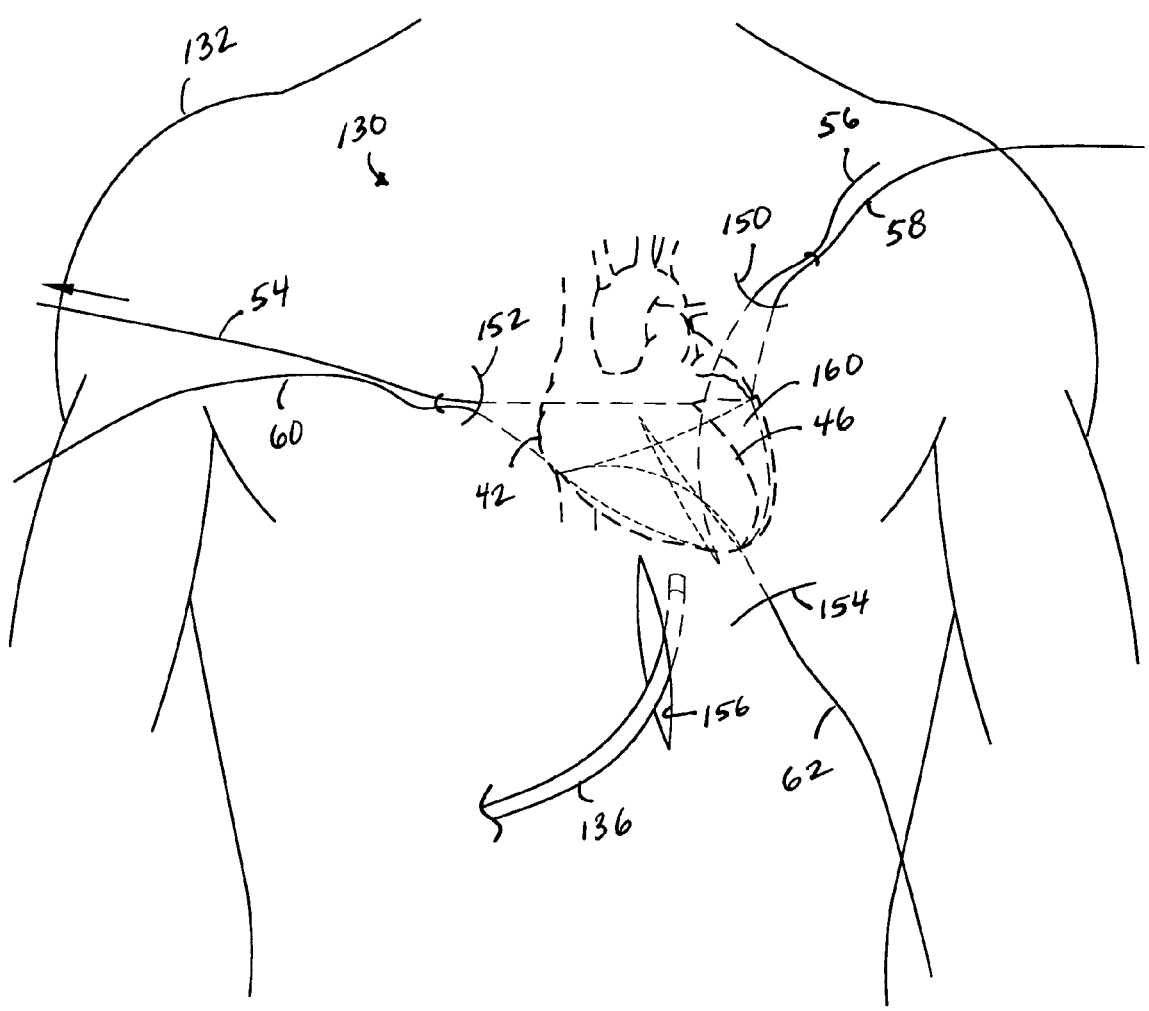

After the device 70 is removed from the thorax 130, and the jacket 32 has the relatively triangular configuration 127 under the heart 42 as shown in FIG. 12, a portion 160 of the jacket 32 is pulled from under the heart 42 to a position up and over the heart 42. In the example shown in FIG. 13, the first anterior strand 54 is pulled which exerts a pulling force on the jacket 32 to pull the first lateral edge 46 and portion 160 of the jacket 32 over the heart 42. The apex strand 62 pulls the jacket apex 40 over the heart apex 44, in the example shown.

Figure 14:
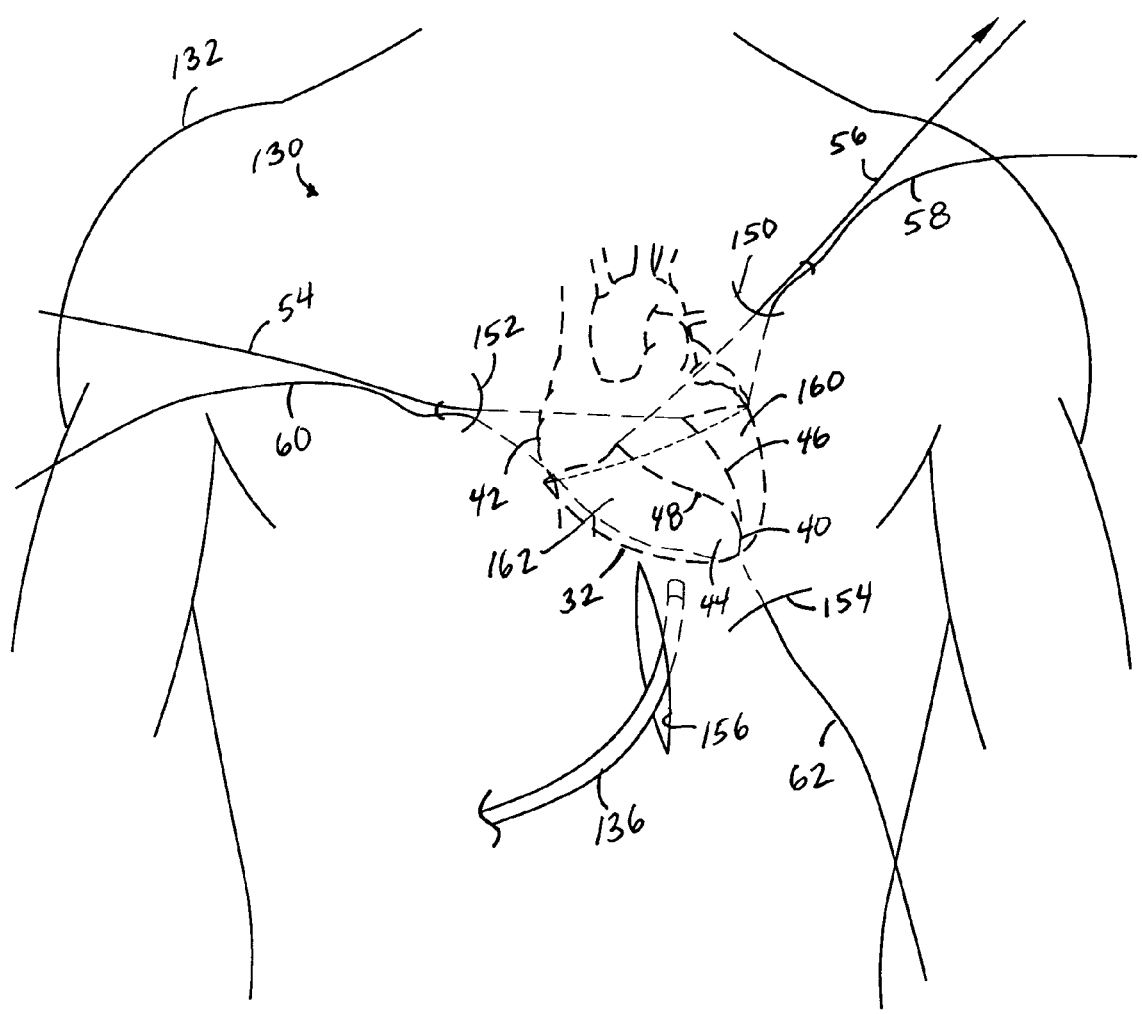

In FIG. 14, the example method illustrated shows pulling the second anterior strand 56 to pull the second lateral edge 48 and another portion 162 of the jacket from a position below the heart 42 to a position around and over the heart 42. The jacket 32 is pulled to position the second lateral edge 48 adjacent to the first lateral edge 46. As can be seen in FIG. 14, after the step of pulling the second anterior strand 56 to pull the second lateral edge 48 over the heart 42 and adjacent to the first lateral edge 46, the jacket 32 is oriented operably over the heart 42 with the apex 40 of the jacket adjacent to and against the heart apex 44.

After the jacket 32 is operably oriented onto the heart 42, the jacket 32 is finally tightened and secured by any means. For example, as shown in FIG. 15, the first lateral edge 46 is sewed or sutured to the second lateral edge 48 to form a seam 164 and to close the slot 50 (FIG. 2). The strands 54, 56, 58, 60 and apex strand 62 are removed (or dissolve over time, if made from dissolvable material), and the incisions 150, 152, 154, 156 are closed.

The above specification and drawings provide a description of example methods and apparatus useable for treating a congestive heart disease. Many embodiments and implementations of the method can be made.

What is claimed is:

1. A method for applying a cardiac support device to a heart of a mammal; the method comprising:
   (a) surgically accessing a heart, including inserting a delivery device into a thorax of the mammal; the delivery device including a cardiac support device having a jacket;
      (i) the jacket comprising a continuous flexible mesh net with a base edge, an opposite apex, first and second lateral edges extending from the base edge, and an open slot between the first and second lateral edges; the slot extending from the base edge and terminating at the apex;
      (ii) the jacket further including:
         (A) a first anterior strand secured to the base edge adjacent to the first lateral edge;
         (B) a second anterior strand secured to the base edge adjacent to the second lateral edge;
         (C) a first posterior strand secured to the base edge and positioned closer to the first anterior strand than to the second anterior strand; and
         (D) a second posterior strand secured to the base edge and positioned closer to the second anterior strand than to the first anterior strand; and
   (b) positioning the jacket around at least a portion of the heart by applying a pulling force to the jacket including pulling each of the first anterior, second anterior, first posterior, and second posterior strands to pull the jacket around the heart.

2. A method according to claim 1 wherein:
   (a) said step of positioning includes:
      (i) pulling in a first direction a first portion of the jacket onto the heart; and then
      (ii) pulling in a second direction a second portion of the jacket onto the heart.

3. A method according to claim 1 wherein:
   (a) said step of positioning includes surgically inserting a tool into the thorax in a position superior to the delivery device.

4. A method according to claim 3 wherein:
   (a) said step of positioning includes using the tool to pull the jacket onto the heart.

5. A method according to claim 4 wherein:
   (a) said step of positioning includes:
      (i) using the tool to pull in a first direction a first portion of the jacket onto the heart; and then
      (ii) using the tool to pull in a second direction a second portion of the jacket onto the heart.

6. A method according to claim 5 wherein:
   (a) said step of using the tool to pull in a second direction includes:
      (i) after using the tool to pull in a first direction a first portion of the jacket onto the heart, removing the tool from the thorax and surgically inserting the tool into another location in the thorax in a position superior to the delivery device.

7. A method according to claim 6 wherein:
   (a) said step of using the tool to pull in a first direction includes grasping one of the first anterior strand, the second anterior strand, the first posterior strand and the second posterior strand; and
   (b) said step of using the tool to pull in a second direction includes grasping another of the first anterior strand, the second anterior strand, the first posterior strand and the second posterior strand.

8. A method according to claim 1 wherein:
   (a) said step of positioning the jacket around at least a portion of the heart includes:
      (i) from a first position superior to the heart, pulling the first posterior strand and the second anterior strand;
         (A) the first posterior strand being pulled under the heart and the second anterior strand being pulled over the heart; and
      (ii) from a second position superior to the heart and lateral to the first position, pulling the second posterior strand and the first anterior strand;
         (A) the second posterior strand being pulled under the heart and the first anterior strand being pulled over the heart.

9. A method according to claim 8 wherein:
   (a) before pulling the first posterior strand and the second anterior strand, surgically inserting a tool through a left intercostal region to the first position and using the tool to pull, individually, the first posterior strand and the second anterior strand; and
   (b) before pulling the second posterior strand and the first anterior strand, surgically inserting the tool through a right intercostal region to the second position and using the tool to pull, individually, the second posterior strand and the first anterior strand.

10. A method according to claim 9 wherein:
    (a) said step of surgically inserting a delivery device into a thorax includes inserting the delivery device into the thorax to a position inferior to an apex of the heart.

11. A method according to claim 10 further including:
    (a) after pulling the first posterior strand, second anterior strand, second posterior strand, and first anterior strand, advancing the delivery device into the thorax to a position under the heart.

12. A method according to claim 11 wherein:
(a) the jacket further includes an apex strand secured to the apex of the jacket; and
(b) after advancing the delivery device, the step of positioning the jacket includes pulling the first posterior strand, second posterior strand, and apex strand.

13. A method according to claim 12 further including:
(a) after the step of advancing the delivery device and pulling the first posterior strand, second posterior strand, and apex strand, removing the delivery device from the thorax.

14. A method according to claim 13 wherein:
(a) after removing the delivery device from the thorax, the step of positioning the jacket includes:
 (i) pulling the first anterior strand to pull the first lateral edge and a portion of the jacket over the heart, and
 (ii) pulling the second anterior strand to pull the second lateral edge of the jacket over the heart and adjacent to the first lateral edge.

15. A method according to claim 14 further including:
(a) after said step of positioning, closing the slot by securing the first lateral edge to the second lateral edge.

16. A method according to claim 1 wherein:
(a) said step of surgically accessing a heart includes performing an intercostal incision and inserting the delivery device;
 (i) the delivery device including a tube with an interior, an open insertion end, and an opposite end;
  (A) the tube including a plurality of notches at the insertion end; each of the first anterior strand, second anterior strand, first posterior strand, and second posterior strand being separately held within a respective one of the notches;
  (B) the jacket being held within the interior of the tube.

* * * * *